US011198016B2

(12) United States Patent
Kim (10) Patent No.: US 11,198,016 B2
(45) Date of Patent: Dec. 14, 2021

(54) IN-VEHICLE AUTOMATED EXTERNAL DEFIBRILLATOR SYSTEM AND METHOD OF CONTROLLING THE SAME

(71) Applicants: HYUNDAI MOTOR COMPANY, Seoul (KR); KIA MOTORS CORPORATION, Seoul (KR)

(72) Inventor: Sun Kyung Kim, Seoul (KR)

(73) Assignees: Hyundai Motor Company, Seoul (KR); Kia Motors Corporation, Seoul (KR)

(*) Notice: Subject to any disclaimer, the term of this patent is extended or adjusted under 35 U.S.C. 154(b) by 187 days.

(21) Appl. No.: 16/513,390

(22) Filed: Jul. 16, 2019

(65) Prior Publication Data
US 2020/0164216 A1    May 28, 2020

(30) Foreign Application Priority Data

Nov. 22, 2018   (KR) .......................... 10-2018-0145595

(51) Int. Cl.
| | |
|---|---|
| *A61N 1/00* | (2006.01) |
| *A61N 1/39* | (2006.01) |
| *A61B 5/18* | (2006.01) |
| *A61N 1/04* | (2006.01) |
| *A61B 5/0205* | (2006.01) |

(Continued)

(52) U.S. Cl.
CPC .............. *A61N 1/3904* (2017.08); *A61B 5/18* (2013.01); *A61N 1/046* (2013.01); *A61N 1/0472* (2013.01); *A61N 1/3931* (2013.01); *A61N 1/3993* (2013.01); *A61B 5/0205* (2013.01); *A61B 5/361* (2021.01); *A61B 5/4836* (2013.01); *A61B 5/6891* (2013.01); *G16H 40/67* (2018.01)

(58) Field of Classification Search
CPC ............ A61N 1/3904; A61N 1/39–395; A61N 1/3931; A61N 1/0472; A61N 1/046; A61N 1/3993; A61B 5/18; A61B 5/6893; A61B 5/6831; A61B 5/0205; A61B 5/6891; A61B 5/4836
See application file for complete search history.

(56) References Cited

U.S. PATENT DOCUMENTS

| | | | | |
|---|---|---|---|---|
| 8,954,129 | B1 * | 2/2015 | Schlegel ................ | A61B 5/282 600/389 |
| 2002/0169482 | A1 * | 11/2002 | SerVaas ................... | A61N 1/39 607/5 |

(Continued)

*Primary Examiner* — Scott M. Getzow
(74) *Attorney, Agent, or Firm* — Morgan, Lewis & Bockius LLP (57) ABSTRACT

An in-vehicle automated external defibrillator system and a method of controlling the same, for detecting a state of a driver and applying an electric shock to his or her heart in the event of emergency, are disclosed. The method of controlling the in-vehicle automated external defibrillator system includes determining, by a driver state recognition device, a state of a driver through a state determination device, upon determining that the driver is in a cardiac arrest state, determining, by a heart impulse position controller, two current pads among a plurality of current pads disposed in a seat belt, determining, by a heart impulse intensity controller, current to be applied through the two determined current pads, and applying, by the heart impulse intensity controller, the determined current through the two determined current pads.

16 Claims, 5 Drawing Sheets

(51) Int. Cl.
*G16H 40/67* (2018.01)
*A61B 5/00* (2006.01)
*A61B 5/361* (2021.01)

(56) References Cited

U.S. PATENT DOCUMENTS

2007/0233197 A1* 10/2007 Jung .................... A61N 1/3904
607/5
2014/0043149 A1* 2/2014 Cowan .................... G16H 40/67
340/12.5
2018/0221648 A1* 8/2018 Gustavson ........... A61N 1/0484
2019/0282822 A1* 9/2019 Freeman ............... A61B 5/6833

* cited by examiner

IN-VEHICLE AUTOMATED EXTERNAL DEFIBRILLATOR SYSTEM AND METHOD OF CONTROLLING THE SAME

This application claims the benefit of Korean Patent Application No. 10-2018-0145595, filed in the Korean Intellectual Property Office on Nov. 22, 2018, which is hereby incorporated by reference as if fully set forth herein.

TECHNICAL FIELD

The present disclosure relates to an in-vehicle automated external defibrillator system and a method of controlling the same for detecting a state of a driver and applying an electric shock to his or her heart in the event of an emergency.

BACKGROUND

In general, when a cardiac arrest occurs in people, it leads to brain damage after 6 to 10 minutes and leads to brain death or death after 10 minutes. Accordingly, when a cardiac arrest occurs, it is required to rapidly perform cardiopulmonary resuscitation or to rapidly apply an impulse to the heart through a defibrillator before getting help from professional rescue workers or a medical institution.

Needless to say, recently, buildings larger than a certain size have come to be equipped with an automated external defibrillator (AED) that is comparatively easy for ordinary people to use even if they do not have sufficient expertise, but there is a problem in that another person is needed around the patient to use the AED.

This problem is more serious in the case of a vehicle driver. In South Korea, the average number of passengers commuting in a single vehicle is about 1.4, which means that the driver rides alone in the majority of vehicles. Accordingly, when a driver suffers a cardiac arrest due to an accident or another reason, it is usually not possible for the driver to receive help from a passenger.

When a driver suffers a cardiac arrest and is not treated immediately, besides the danger faced by the driver, there is the risk of a secondary accident involving pedestrians or other vehicles around the vehicle in question.

SUMMARY

Accordingly, the present disclosure is directed to an in-vehicle automated external defibrillator system and a method of controlling the same that substantially obviates one or more problems due to limitations and disadvantages of the related art.

An object of the present disclosure is to provide an in-vehicle automated external defibrillator system and a method of controlling the same for enabling immediate treatment when a state of a driver is detected and a cardiac arrest occurs in a vehicle.

Additional advantages, objects, and features of the present disclosure will be set forth in part in the description which follows and in part will become apparent to those having ordinary skill in the art upon examination of the following or may be learned from practice of the invention. The objectives and other advantages of the present disclosure may be realized and attained by the structure particularly pointed out in the written description and claims hereof as well as the appended drawings.

To achieve these objects and other advantages and in accordance with the purpose of the present disclosure, as embodied and broadly described herein, a method of controlling an in-vehicle automated external defibrillator system includes determining, by a driver state recognition device, a state of a driver through a state determination device, upon determining that the driver is in a cardiac arrest state, determining, by a heart impulse position controller, two current pads among a plurality of current pads disposed in a seat belt, determining, by a heart impulse intensity controller, current to be applied through the two determined current pads, and applying, by the heart impulse intensity controller, the determined current through the two determined current pads.

In another aspect of the present disclosure, an in-vehicle automated external defibrillator system includes a state determination device configured to acquire information for determining a state of a driver, a driver state recognition device configured to determine the state of the driver based on the information acquired through the state determination device, a heart impulse position controller configured to determine two current pads among a plurality of current pads disposed in a seat belt when the driver state recognition device determines the driver to be in a cardiac arrest state, and a heart impulse intensity controller configured to determine current to be applied through the two determined current pads and to apply the determined current through the two determined current pads.

BRIEF DESCRIPTION OF THE DRAWINGS

The accompanying drawings, which are included to provide a further understanding of the present disclosure and are incorporated in and constitute a part of this application, illustrate embodiment(s) of the present disclosure and together with the description serve to explain the principle of the invention. In the drawings.

DETAILED DESCRIPTION

Exemplary embodiments of the present disclosure are described in detail so as for those of ordinary skill in the art to easily implement with reference to the accompanying drawings. However, the present disclosure may be implemented in various different forms and is not limited to these embodiments. To clearly describe the present disclosure, a part without concerning to the description is omitted in the drawings, and like reference numerals in the specification denote like elements.

In addition, when a certain part "includes" a certain component, this indicates that the part may further include another component instead of excluding another component unless there is no different disclosure. The same reference numbers will be used throughout the drawings and the specification to refer to the same parts.

According to an embodiment of the present disclosure, when a state of a driver in a vehicle is detected and a cardiac arrest state is detected, a heart impulse may be immediately applied through a current pad included in a seat belt.

Figure 1:
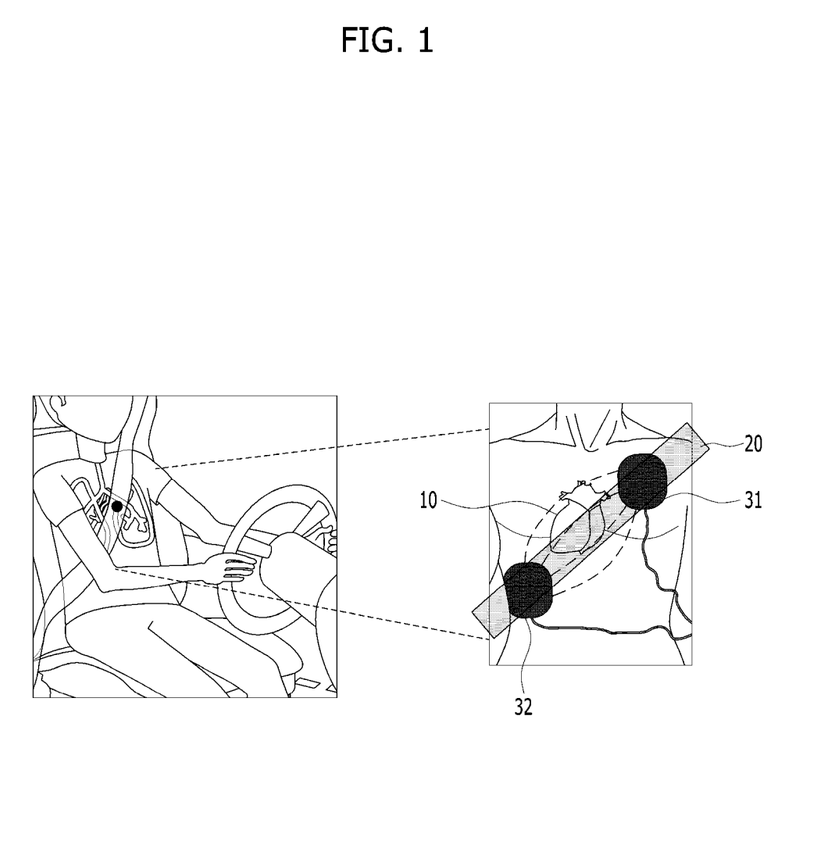
FIG. 1 is a diagram for explanation of a concept of an operation of an in-vehicle automated external defibrillator system according to an embodiment of the present disclosure.

FIG. 1 is a diagram for explanation of a concept of an operation of an in-vehicle automated external defibrillator system according to an embodiment of the present invention.

In general, an automated external defibrillator (AED) is configured in such a way that two current pads are attached across the heart to allow current discharged from the current pads to be transmitted through the heart, thereby helping a driver recover from the cardiac arrest state. In this case, generally, in the case of infants, respective current pads are attached to the front and rear surfaces of the upper body but, in the case of adults, the current pads are attached to the chest at one side and the flank at the other side.

Referring to FIG. 1, a device that is the most adjacent to positions to which the current pads of the AED in a vehicle are attached and that maintains such positions at ordinary times may be a seat belt 20. This is because the majority of recently released vehicles continuously output a warning sound when the seat belt of a driver seat is not fastened, drivers are required to fasten the seat belt according to the law, and drivers always fasten the seat belt 20 for personal safety while driving a vehicle. Accordingly, an automated external defibrillator system according to an embodiment may be configured in such a way that two current pads 31 and 32 are spaced apart from each other so as to allow the heart 10 to be positioned between two current pads 31 and 32 under the seat belt 20 in order to allow current to be transmitted through the heart 10.

Figure 2:
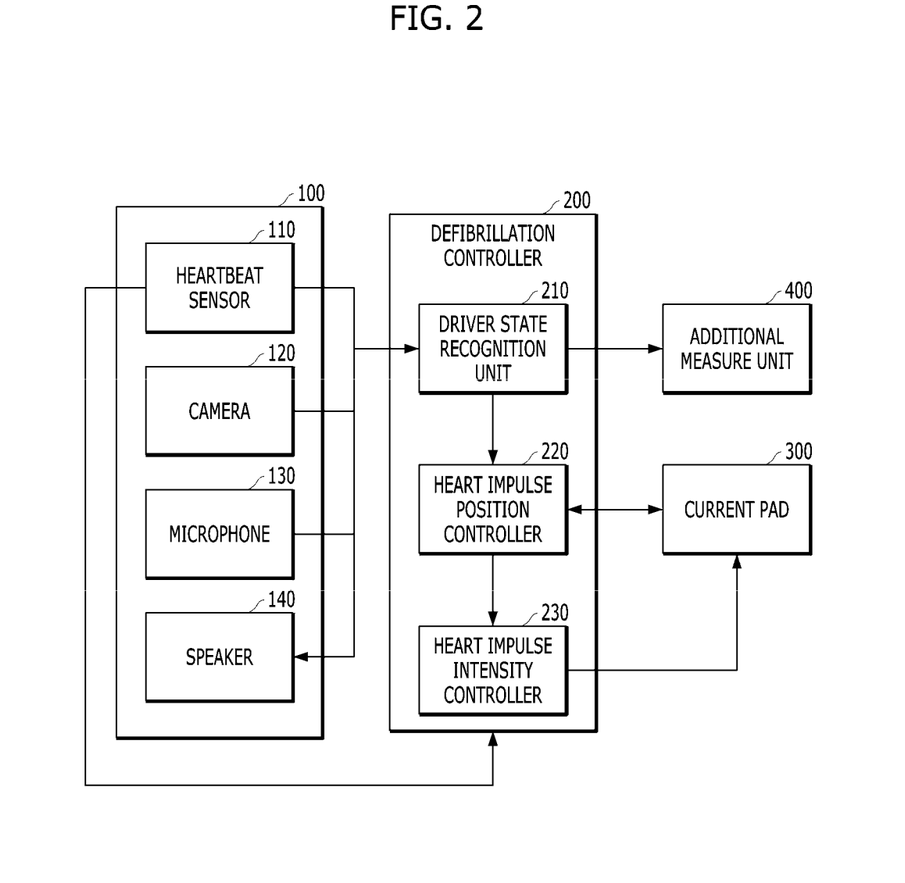
FIG. 2 is a block diagram showing an example of the configuration of an in-vehicle automated external defibrillator system according to an embodiment of the present disclosure.

FIG. 2 is a block diagram showing an example of the configuration of an in-vehicle automated external defibrillator system according to an embodiment of the present disclosure.

Referring to FIG. 2, the in-vehicle automated external defibrillator system may include a state determination device 100 for determining a state of a driver, a defibrillation controller 200 for determining a heart impulse position and impulse intensity through a current pad 300 upon determining a driver to be in a cardiac arrest state based on information collected by the state determination device 100, the plurality of current pads 300 for supplying current corresponding to the position and intensity determined by the defibrillation controller 200 to a passenger, and an additional measure device 400 for taking additional measure other than the heart impulse in the cardiac arrest state of the driver. Hereinafter, each component will be described in more detail.

First, the state determination device 100 may include a heartbeat sensor 110 for measuring a heartbeat state of a driver, a camera 120 for acquiring an image of the driver, a microphone 130 for receiving sound in a vehicle, and a speaker 140 for outputting sound.

The heartbeat sensor 110 is not limited with regard to the position and constitution thereof, as long as the heartbeat sensor 110 is capable of measuring the heartbeat state of a driver. For example, the heartbeat sensor 110 may be a Doppler-type heartbeat sensor installed in the back of a sheet or in the seat belt, may be an electrocardiogram sensor disposed in a steering wheel, or may include two or more sensors for measurement accuracy.

It may be sufficient to dispose the camera 120 at a position for acquiring an image of a driver. For example, the camera 120 may be an in-cabin camera, but is not limited thereto.

It may be sufficient to dispose the microphone 130 at a position for at least receiving the voice of the driver.

The defibrillation controller 200 may include a driver state recognition unit 210 for determining whether a driver suffers a cardiac arrest using the state determination device 100, a heart impulse position controller 220 for determining a current pad to be used for a heart impulse among the plurality of current pads 300, and a heart impulse intensity controller 230 for determining the intensity of energy to be applied through the current pad.

In detail, the driver state recognition unit 210 may output a voice message that prompts the driver to respond through the speaker 140 when detecting a cardiac arrest through the heartbeat sensor 110 and determining the abnormal state of the driver from an image captured by the camera 120, and may determine the driver to be in a cardiac arrest state when a driver voice corresponding to the sound message is not detected by the microphone 130 (i.e., unconsciousness). Here, the abnormal state of the driver determined from the image captured by the camera 120 may include the case in which failure to look forward or total absence of movement is detected from an image captured through an in-cabin camera, the case in which an abnormal driving behavior such as continuous lane departure is detected through a front camera or a vision sensor, and the like.

Upon determining a cardiac arrest through the driver state recognition unit 210, the heart impulse position controller 220 may determine the two current pads that are at optimum positions for transmitting current to the heart of a driver among the plurality of current pads 300, in consideration of the body type of the driver.

The heart impulse intensity controller 230 may determine intensity of current supposed to flow for a heart impulse in consideration of electric resistance at the positions of the two current pad, which are determined through the heart impulse position controller 220, and electric resistance when the current pads are attached directly to the skin and may supply current with the determined intensity to the corresponding current pad.

Figure 3:
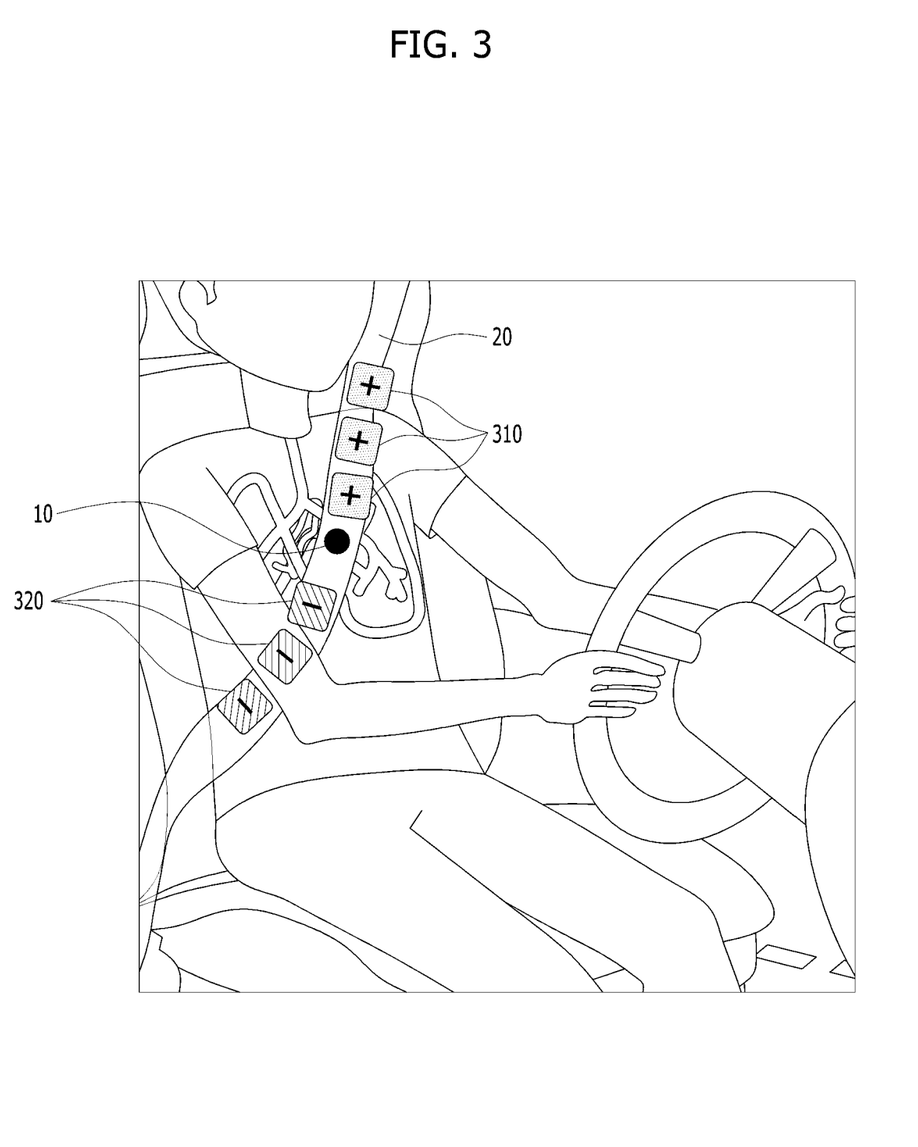
FIG. 3 illustrates an example of arrangement of a current pad according to an embodiment of the present disclosure.

The arrangement of the current pad 300 will be described with reference to FIG. 3. FIG. 3 illustrates an example of arrangement of a current pad according to an embodiment of the present disclosure. Referring to FIG. 3, a plurality of current pads that are spaced apart from each other in an extension direction of the seat belt 20 may be disposed on a surface of the seat belt 20, which contacts the body of the driver. Here, the plurality of current pads may include a plurality of first electrode current pads 310 and a plurality of second electrode current pads 320 having opposite polarity to the first electrode. For example, when the first electrode current pad is a positive (+) electrode, the second electrode current pad may be a negative (−) electrode. On the other hand, when the first electrode current pad is a negative (−) electrode, the second electrode current pad may be a positive (+) electrode.

Pads with the same polarity may be disposed adjacent to each other, and the first electrode current pads 310 and the second electrode current pads 320 may be disposed to position the heart 10 between the two pads 310 and 320 when the seat belt 20 for a driver with a standard somatotype is fastened as shown in FIG. 3, but this is exemplary and the present disclosure is not limited thereto.

Referring back to FIG. 2, when the aforementioned driver state recognition unit 210 determines that the driver has suffered a cardiac arrest, the additional measure device 400 may take additional measures other than providing a heart impulse. Examples of the additional measures may include hazard light flashing, stopping on the shoulder via autonomous driving, or emergency relief signal transmission. To this end, the additional measure device 400 may include at least one of an autonomous driving controller, a body controller, or a telematics system, but this is exemplary and the additional measure device 400 is not limited to any vehicular configuration as long as the additional measure device 400 performs a function for prevention of secondary accidents and requesting a rescue.

Figure 4:
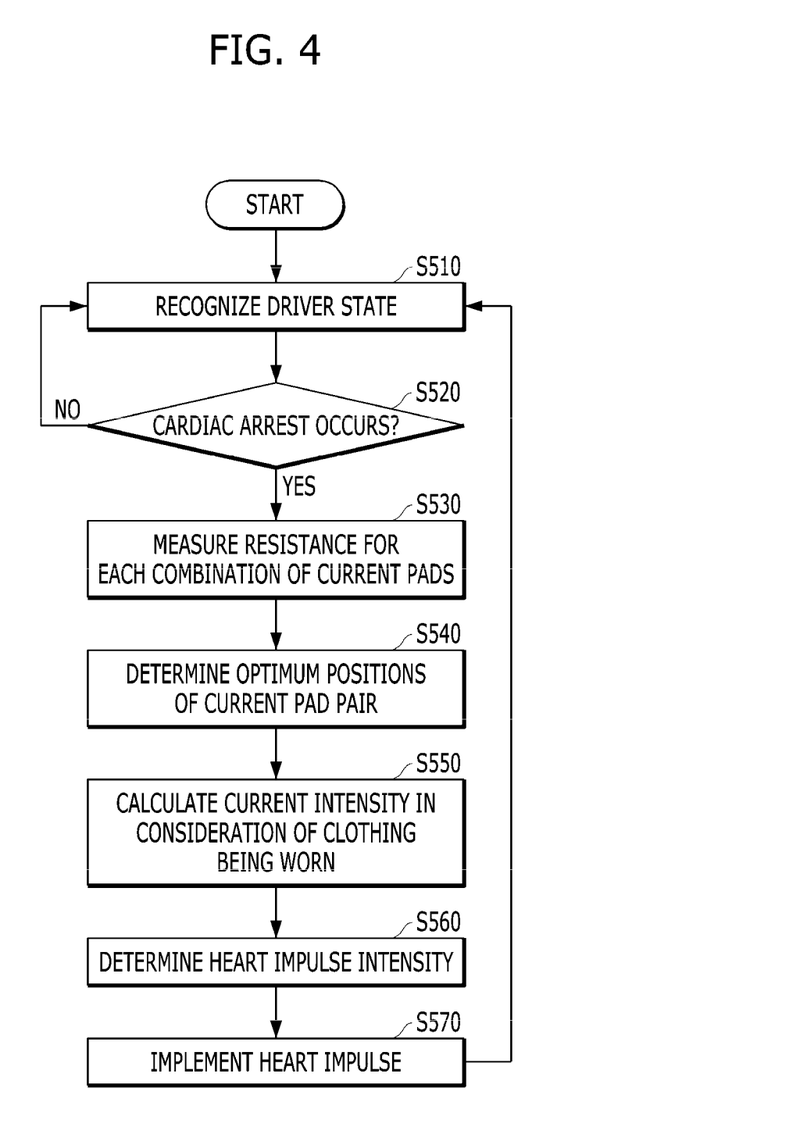
FIG. 4 is a flowchart showing an example of a method of controlling an in-vehicle automated external defibrillator system according to an embodiment of the present disclosure.

FIG. 4 is a flowchart showing an example of a method of controlling an in-vehicle automated external defibrillator system according to an embodiment of the present disclosure.

Referring to FIG. 4, first, a state of a driver may be recognized (S510). As described above, the driver state recognition procedure may be performed in such a way that the driver state recognition unit 210 may output a voice message that prompts the driver to respond through the speaker 140 when detecting a cardiac arrest through the heartbeat sensor 110 and determining an abnormal state of the driver from an image captured by the camera 120, and may determine the driver to be in a cardiac arrest state when a driver voice corresponding to the sound message is not detected from the microphone 130 (i.e., unconsciousness).

As the state recognition result, when a cardiac arrest occurs (YES of S520), the heart impulse position controller 220 may measure resistance for each combination of current pads in order to determine two pads (i.e., one first electrode pad and one second electrode pad) that are the most appropriate for applying an impulse to the heart of the driver among the plurality of current pads 300 (S530). For example, as shown in FIG. 3, when the number of first electrode current pads 310 is 3 and the number of second electrode current pads 320 is 3, it may be possible to make total of 9 combinations, and electric resistance between pads may be measured for each combination.

The heart impulse position controller 220 may determine optimum positions of a current pad pair based on the measurement result of the electric resistance between the pads (S540). For example, the heart impulse position controller 220 may determine the combination having the lowest electric resistance to be the optimum current pad pair.

Then, the heart impulse intensity controller 230 may calculate current intensity in consideration of clothing being worn (S550). This is because amplitude of current, which effectively acts on the heart, is changed depending on the type and thickness of clothes that a driver wears even if the same current is applied. The current procedure may include a procedure of comparing electric resistance of the body when a current pad is attached directly to the skin with electric resistance on clothes that the driver wears. For example, current for a heart impulse may be obtained through a procedure according to Equation 1 below.

$$I_{Heart\ Impulse} = \frac{V_{Skin}}{R_{Skin}} = \frac{V_{On\ Clothes}}{R_{On\ Clothes}}$$ [Equation 1]

Here, when the current pad is attached directly to the skin, the electric resistance and voltage value of the body may be measured in advance using a predetermined procedure, a resistance value on clothes that the driver wears may be a resistance value measured in operation S530, and each voltage value may be a voltage applied to the body of the driver, including the skin or the clothes, across the two current pads.

The heart impulse intensity controller 230 may determine final heart impulse intensity based on current intensity in consideration of clothes (S560) and may supply current corresponding to the determined intensity to a pre-determined current pad pair to implement application of a heart impulse (S570).

After application of a heart impulse is performed, the aforementioned procedure may be repeatedly preformed. For example, after application of a heart impulse is performed, a state of the driver may be recognized again, and when a cardiac arrest state is not overcome, a heart impulse may be applied again. In addition, as the number of times that a heart impulse is applied is increased, supplied current may be increased by a predetermined ratio based on the previous time.

According to another embodiment of the present disclosure, the current pad may not be disposed in the seat belt, which will be described with reference to FIG. 5.

Figure 5:
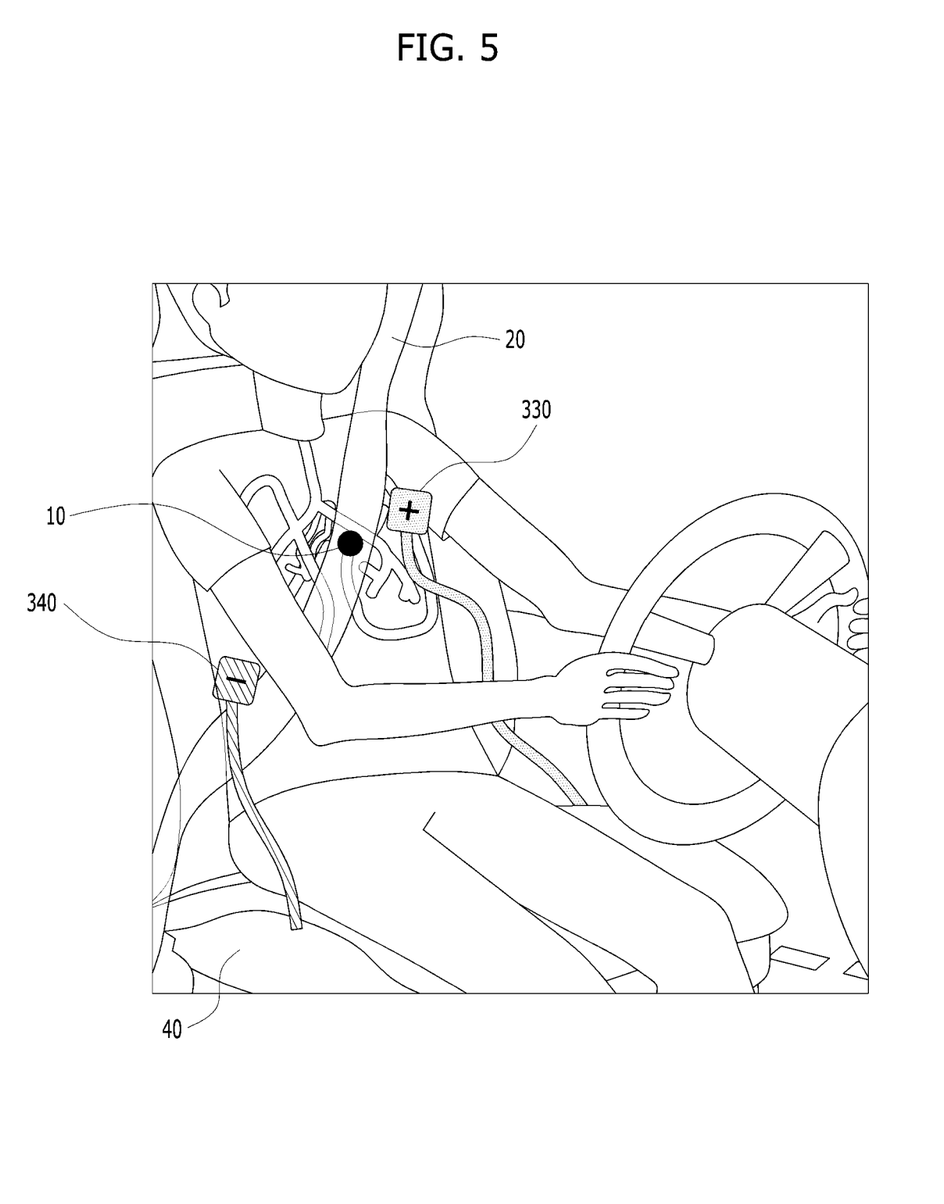
FIG. 5 illustrates an example of arrangement of current pads of an in-vehicle automated external defibrillator system according to another embodiment of the present disclosure.

FIG. 5 illustrates an example of arrangement of current pads of an in-vehicle automated external defibrillator system according to another embodiment of the present disclosure.

Referring to FIG. 5, at least one first electrode pad 330 and at least one second electrode pad 340 may be disposed at positions that are not related to the seat belt 20. For example, the first electrode pad 330 and the second electrode pad 340 may be accommodated in a sheet 40. In the event of an emergency, a passenger may directly attach the first electrode pad 330 and the second electrode pad 340 at appropriate positions. In this case, similarly to an AED, a state of a driver and intensity of current may also be determined by the in-vehicle automated external defibrillator system according to an embodiment, and the passenger may directly determine the time point at which to apply current.

The above configured in-vehicle automated external defibrillator system and a method of controlling the same according to at least one embodiment of the present disclosure may rapidly and accurately apply a heart impulse within a so-called "golden hour" by detecting a cardiac arrest of the driver.

In addition, secondary accidents resulting from inability of a driver to drive may be prevented.

It will be appreciated by persons skilled in the art that that the effects that could be achieved with the present invention are not limited to what has been particularly described hereinabove and other advantages of the present invention will be more clearly understood from the detailed description.

The aforementioned present disclosure can also be embodied as computer readable code/algorithm/software stored on a non-transitory computer readable recording medium. The computer readable recording medium is any data storage device that can store data which can thereafter be read by a computer, a processor/microprocessor, the state determination device and/or components thereof, and the defibrillation controller and/or components thereof. Examples of the computer readable recording medium include a hard disk drive (HDD), a solid state drive (SSD), a silicon disc drive (SDD), read-only memory (ROM), random-access memory (RAM), CD-ROM, magnetic tapes, floppy disks, optical data storage devices, etc. The state determination device and/or the components thereof may include one or more processors/microprocessors and/or a non-transitory computer readable recording medium storing a program/code/algorithm/software, and the defibrillation controller and/or components thereof include one or more processors/microprocessors and/or a non-transitory computer readable recording medium storing a program/code/algorithm/software. As an alternative, the state determination device and the defibrillation controller may together include one or more processors/microprocessors and/or a non-transitory computer readable recording medium storing a program/code/algorithm/software. Such processor(s) or microprocessor(s) may perform the above described functions, operations, steps, etc., by executing the computer readable program/code/algorithm/software stored on the non-transitory computer readable recording medium.

It will be apparent to those skilled in the art that various modifications and variations can be made in the present disclosure without departing from the spirit or scope of the invention. Thus, it is intended that the present disclosure cover the modifications and variations of this disclosure provided they come within the scope of the appended claims and their equivalents.

What is claimed is:

1. A method of controlling an in-vehicle automated external defibrillator system, the method comprising:
   determining, by a driver state recognition device, a state of a driver through a state determination device;
   upon determining that the driver is in a cardiac arrest state, determining, by a heart impulse position controller, two current pads among a plurality of current pads disposed in a seat belt;
   determining, by a heart impulse intensity controller, current to be applied through the two determined current pads; and
   applying, by the heart impulse intensity controller, the determined current through the two determined current pads,
   wherein:
   the plurality of current pads include a plurality of first electrode pads and a plurality of second electrode pads,
   the plurality of first electrode pads are sequentially disposed adjacent to each other along an extension direction of the seat belt and the plurality of second electrode pads are sequentially disposed adjacent to each other along the extension direction,
   the determining the two current pads includes measuring resistance between pads for each combination of the plurality of first electrode pads and the plurality of second electrode pads,
   the determining the current includes calculating an intensity of current in consideration of clothing being worn by the driver, and
   the calculating intensity of current in consideration of clothing being worn includes comparing a pre-stored skin resistance and the measured resistance.

2. The method of claim 1, wherein:
   the state determination device includes at least one of a heartbeat sensor configured to detect a heartbeat state of the driver or a camera configured to acquire an image of the driver; and
   the driver state recognition device determines whether the driver is in the cardiac arrest state based on at least one of whether the cardiac arrest state is detected through the heartbeat sensor or whether failure to look forward or total absence of movement is detected from the image of the driver, captured through the camera.

3. The method of claim 2, wherein:
   the state determination device further includes a microphone and a speaker; and
   the driver state recognition device outputs a message that prompts the driver to respond through the speaker when detecting the cardiac arrest state through the heartbeat sensor and detecting failure to look forward or total absence of movement from the image of the driver, captured by the camera, and determines the driver to be in the cardiac arrest state when a response to the message is not input through the microphone.

4. The method of claim 1, wherein:
   the determining the two current pads further includes:
   determining a first electrode pad and a second electrode pad, corresponding to a combination having a lowest measured resistance therebetween, as the two current pads.

5. The method of claim 4, wherein the plurality of first electrode pads and the plurality of second electrode pads are spaced apart from each other in the extension direction of the seat belt on a surface of the seat belt, which contacts a body of the driver.

6. The method of claim 1, further comprising determining the state of the driver again after applying the determined current through the two determined current pads.

7. The method of claim 1, further comprising: performing at least one of hazard light flashing, stopping on the shoulder via autonomous driving, or emergency relief signal transmission through an additional measure device upon determining the driver to be in the cardiac arrest state.

8. A non-transitory computer readable recording medium having recorded thereon a program for executing the method of controlling the in-vehicle automated external defibrillator system of claim 1.

9. An in-vehicle automated external defibrillator system comprising:
   a state determination device configured to acquire information for determining a state of a driver;
   a driver state recognition device configured to determine the state of the driver based on the information acquired through the state determination device;
   a heart impulse position controller configured to determine two current pads among a plurality of current pads disposed in a seat belt when the driver state recognition device determines the driver to be in a cardiac arrest state; and
   a heart impulse intensity controller configured to determine current to be applied through the two determined current pads and to apply the determined current through the two determined current pads,
   wherein:
   the plurality of current pads include a plurality of first electrode pads and a plurality of second electrode pads,
   the plurality of first electrode pads are sequentially disposed adjacent to each other along an extension direction of the seat belt and the plurality of second electrode pads are sequentially disposed adjacent to each other along the extension direction,
   the heart impulse position controller measures resistance between pads for each combination of the plurality of first electrode pads and the plurality of second electrode pads, and
   the heart impulse intensity controller compares a pre-stored skin resistance and the measured resistance to calculate an intensity of current in consideration of clothing being worn by the driver.

10. The in-vehicle automated external defibrillator system of claim 9, wherein:

the state determination device includes at least one of a heartbeat sensor configured to detect a heartbeat state of the driver or a camera configured to acquire an image of the driver; and the driver state recognition device determines whether the driver is in the cardiac arrest state based on at least one of whether the cardiac arrest state is detected through the heartbeat sensor or whether failure to look forward or total absence of movement is detected from the image of the driver, captured through the camera.

11. The in-vehicle automated external defibrillator system of claim 10, wherein:

the state determination device further includes a microphone and a speaker; and the driver state recognition device outputs a message that prompts the driver to respond through the speaker when detecting the cardiac arrest state through the heartbeat sensor and detecting failure to look forward or total absence of movement from the image of the driver, captured by the camera, and determines the driver to be in the cardiac arrest state when a response to the message is not input through the microphone.

12. The in-vehicle automated external defibrillator system of claim 9, wherein:

the heart impulse position controller determines a first electrode pad and a second electrode pad, corresponding to a combination having a lowest measured resistance therebetween, as the two current pads.

13. The in-vehicle automated external defibrillator system of claim 12, wherein the plurality of first electrode pads and the plurality of second electrode pads are spaced apart from each other in the extension direction of the seat belt on a surface of the seat belt, which contacts a body of the driver.

14. The in-vehicle automated external defibrillator system of claim 9, wherein the driver state recognition device determines the state of the driver again after the determined current is applied.

15. The in-vehicle automated external defibrillator system of claim 9, further comprising an additional measure device configured to perform at least one of hazard light flashing, stopping on the shoulder via autonomous driving, or emergency relief signal transmission upon determining the driver to be in the cardiac arrest state.

16. The in-vehicle automated external defibrillator system of claim 9, wherein the plurality of second electrode current pads have an opposite polarity to the plurality of first electrode current pads;

each of the plurality of second electrode current pads are disposed only on one side of one of the plurality of first electrode current pads which is adjacent to one of the plurality of second electrode current pads; and each of the plurality of first electrode current pads are disposed only on one side of the one of the plurality of second electrode current pads.

* * * * *